US012770263B2

(12) United States Patent
Kanakatte Gurumurthy et al.

(10) Patent No.: US 12,770,263 B2
(45) Date of Patent: Oct. 20, 2026

(54) METHOD AND SYSTEM FOR HEALTH ESTIMATION OF BODY IMPLANTS

(71) Applicant: Tata Consultancy Services Limited, Mumbai (IN)

(72) Inventors: Aparna Kanakatte Gurumurthy, Bangalore (IN); Divya Manoharlal Bhatia, Bangalore (IN); Rupsha Mukherjee, Kolkata (IN); Jayavardhana Rama Gubbi Lakshminarasimha, Bangalore (IN); Murali Poduval, Thane West (IN); Avik Ghose, Kolkata (IN)

(73) Assignee: Tata Consultancy Services Limited, Mumbai (IN)

( * ) Notice: Subject to any disclaimer, the term of this patent is extended or adjusted under 35 U.S.C. 154(b) by 182 days.

(21) Appl. No.: 18/973,685

(22) Filed: Dec. 9, 2024

(65) Prior Publication Data

US 2025/0209628 A1 Jun. 26, 2025

(30) Foreign Application Priority Data

Dec. 20, 2023 (IN) ............................ 202321087213

(51) Int. Cl.
*G06T 7/00* (2017.01)
*A61F 2/32* (2006.01)
(Continued)

(52) U.S. Cl.
CPC .............. *G06T 7/0016* (2013.01); *A61F 2/32* (2013.01); *A61F 2/468* (2013.01); *G06T 7/60* (2013.01);
(Continued)

(58) Field of Classification Search
CPC .......... G06T 7/0016; G06T 7/60; G06T 7/73; G06T 2200/28; G06T 2207/10116;
(Continued)

(56) References Cited

U.S. PATENT DOCUMENTS

| | | | | |
|---|---|---|---|---|
| 8,644,568 | B1 * | 2/2014 | Hoffmann | G16H 50/50 382/128 |
| 9,675,273 | B2 * | 6/2017 | Gluncic | A61B 5/066 |

(Continued)

*Primary Examiner* — Claire X Wang
(74) *Attorney, Agent, or Firm* — Finnegan, Henderson, Farabow, Garrett & Dunner LLP

(57) ABSTRACT

Existing approaches in this domain are targeted to identifying specific anomalies, and there is no system available that determines implant health comprehensively by considering various aspects that may represent health of the implants. The method and system disclosed herein provide an implant health monitoring approach in which by processing an X-ray image received as input, a system identifies location of an implant in body of a subject, and identifies manufacturer and subtype details of the implant. Further, an implant size and implant fixation details are determined. Further, anomaly detection is performed to determine presence of one or more anomalies in the implant, based on the determined manufacturer and subtype details, the determined location of the implant, a determined region around the implant, the implant fixation details, and the implant size information, and accordingly the implant is classified as one of Faulty, Healthy, and Probable faulty.

9 Claims, 4 Drawing Sheets

200

FIG. 2

(51) Int. Cl.

| | |
|---|---|
| ***A61F 2/46*** | (2006.01) |
| ***G06T 7/60*** | (2017.01) |
| ***G06T 7/73*** | (2017.01) |
| ***G06V 10/764*** | (2022.01) |

(52) U.S. Cl.
CPC .............. *G06T 7/73* (2017.01); *G06V 10/764* (2022.01); *G06T 2200/28* (2013.01); *G06T 2207/10116* (2013.01); *G06T 2207/30008* (2013.01); *G06V 2201/033* (2022.01)

(58) Field of Classification Search
CPC . G06T 2207/30008; G06T 2207/30052; G06T 7/0012; A61F 2/32; A61F 2/468; G06V 10/764; G06V 2201/033; A61B 5/4851; A61B 6/12
See application file for complete search history.

(56) References Cited

U.S. PATENT DOCUMENTS

| | | | |
|---|---|---|---|
| 2012/0189543 | A1 | 7/2012 | Wang et al. |
| 2018/0160971 | A1 | 6/2018 | Giphart et al. |

* cited by examiner

METHOD AND SYSTEM FOR HEALTH ESTIMATION OF BODY IMPLANTS

PRIORITY CLAIM

The present application claims priority to Indian Application No. 202321087213, filed on Dec. 20, 2023. The entire contents of the aforementioned application are incorporated herein by reference.

TECHNICAL FIELD

The disclosure herein generally relates to image processing, and, more particularly, to a method and system for health estimation of body implants.

BACKGROUND

The implanted prosthesis may need to be repaired or replaced over years due to wear and tear. Different prosthesis models require different procedures and sometimes different equipment for repair and removal. In addition, these prostheses are followed up over many years to track signs of anomalies of different types, which, if not treated on time, may cause/trigger health issues. Monitoring these implants thus becomes critical in the long term to enable early effective interventions.

Implant health denotes the changes that may occur in the implant and/or its surrounding bone over a period including wear, aseptic loosening, breakage, dislocation, fracture and subsidence or change in position. These are specially applicable to total joint implants as they are expected to stay in the body for an extended period of time and have a finite risk of revision after having been used for a number of years. The causes for failure have been defined as wear, aseptic loosening, septic loosening, breakage, subsidence and change in position, dislocations, and periprosthetic fractures.

Existing approaches in this domain are targeted to identifying specific anomalies, and there is no system available that determines implant health comprehensively by considering various aspects that may represent health of the implants.

SUMMARY

Embodiments of the present disclosure present technological improvements as solutions to one or more of the above-mentioned technical problems recognized by the inventors in conventional systems. For example, in one embodiment, a processor implemented method is provided. The method includes obtaining an X-ray image as input. Further, location of an implant in body of a subject is determined by performing implant region localization on the X-ray image. Further, a manufacturer and subtype details of the implant is determined by analyzing the located implant. Further, an implant size is determined by performing a landmark analysis on the located implant. Further, an implant fixation data with respect to the implant is determined by analyzing the located implant. Further, an anomaly detection is performed to determine presence of one or more anomalies in the implant, based on the determined manufacturer and subtype details, the determined location of the implant, a determined region around the implant, the implant fixation data, and the implant size information. Further, health of the implant is classified as one of Faulty, Healthy, and Probable faulty, based on the determined presence of anomalies.

In an aspect of the method, performing the implant region localization comprises: determining, after verifying that the X-ray image is fit for processing, presence of the implant in the X-ray image; selecting one or more regions around the implant with a pre-defined margin to include a bone region; and processing the X-ray image after selecting the one or more regions around the implant, using a multilevel classification network to classify one or more areas in the image into implant region, bone region, and one or more other regions.

In another aspect of the method, the one or more anomalies comprises implant loosening, and implant breakage, wherein, the implant loosening is determined based on one of a) presence of radiolucency around the implant, and b) a metrics based data from one or more history images, and the implant breakage is determined based on one of a) a) template based anomaly detection, and b) one or more image processing algorithms.

In another aspect, a system is provided. The system includes one or more hardware processors, a communication interface, and a memory storing a plurality of instructions. The plurality of instructions cause the one or more hardware processors to obtain an X-ray image as input. Further, location of an implant in body of a subject is determined by performing implant region localization on the X-ray image. Further, a manufacturer and subtype details of the implant is determined by analyzing the located implant. Further, an implant size is determined by performing a landmark analysis on the located implant. Further, an implant fixation data with respect to the implant is determined by analyzing the located implant. Further, an anomaly detection is performed to determine presence of one or more anomalies in the implant, based on the determined manufacturer and subtype details, the determined location of the implant, a determined region around the implant, the implant fixation data, and the implant size information. Further, health of the implant is classified as one of Faulty, Healthy, and Probable faulty, based on the determined presence of anomalies.

In an aspect of the system, the one or more hardware processors are configured to perform the implant region localization by: determining, after verifying that the X-ray image is fit for processing, presence of the implant in the X-ray image; selecting one or more regions around the implant with a pre-defined margin to include a bone region; and processing the X-ray image after selecting the one or more regions around the implant, using a multilevel classification network to classify one or more areas in the image into implant region, bone region, and one or more other regions.

In another aspect of the system, the one or more anomalies comprises implant loosening, and implant breakage, wherein, the implant loosening is determined based on one of a) presence of radiolucency around the implant, and b) a metrics based data from one or more history images, and the implant breakage is determined based on a template based anomaly detection, and one or more image processing algorithms.

In yet another aspect, a non-transitory computer readable medium is provided. The non-transitory computer readable medium includes a plurality of instructions, which when executed, cause the one or more hardware processors to obtaining an X-ray image as input. Further, location of an implant in body of a subject is determined by performing implant region localization on the X-ray image. Further, a manufacturer and subtype details of the implant is determined by analyzing the located implant. Further, an implant size is determined by performing a landmark analysis on the located implant. Further, an implant fixation data with respect to the implant is determined by analyzing the located implant. Further, an anomaly detection is performed to determine presence of one or more anomalies in the implant, based on the determined manufacturer and subtype details, the determined location of the implant, a determined region around the implant, the implant fixation data, and the implant size information. Further, health of the implant is classified as one of Faulty, Healthy, and Probable faulty, based on the determined presence of anomalies.

In yet another aspect of the non-transitory computer readable medium, performing the implant region localization comprises: determining, after verifying that the X-ray image is fit for processing, presence of the implant in the X-ray image; selecting one or more regions around the implant with a pre-defined margin to include a bone region; and processing the X-ray image after selecting the one or more regions around the implant, using a multilevel classification network to classify one or more areas in the image into implant region, bone region, and one or more other regions.

In yet another aspect of the non-transitory computer readable medium, the one or more anomalies comprises implant loosening, and implant breakage, wherein, the implant loosening is determined based on one of a) presence of radiolucency around the implant, and b) a metrics based data from one or more history images, and the implant breakage is determined based on a template based anomaly detection, and one or more image processing algorithms.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

DETAILED DESCRIPTION

Figure 1:
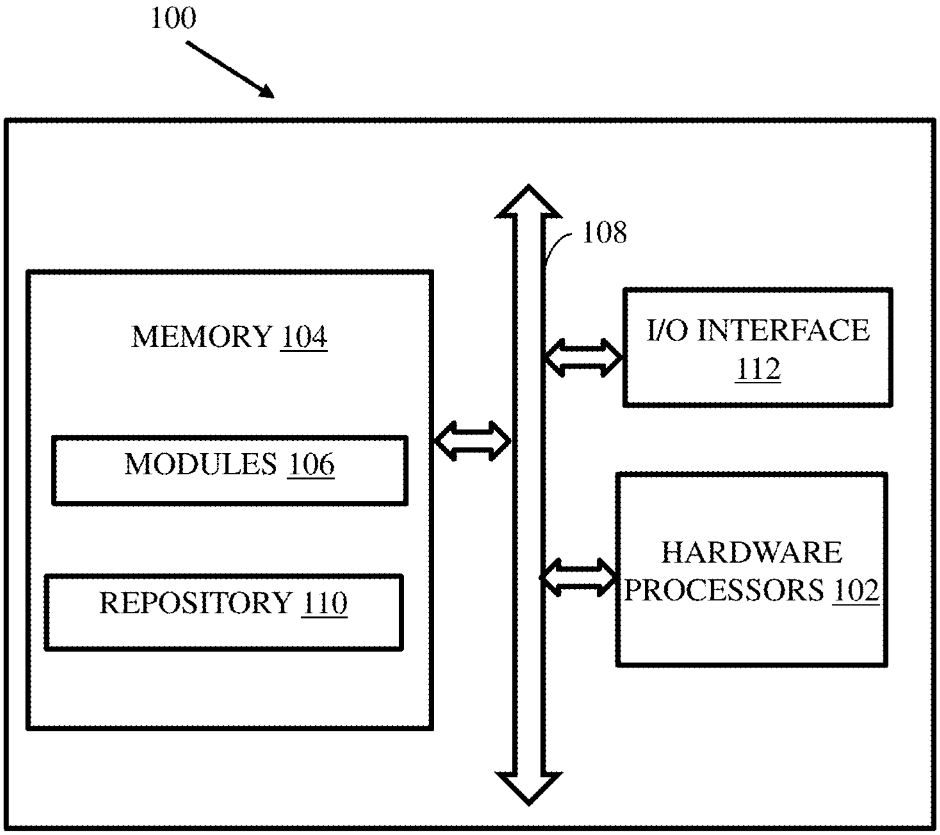
FIG. 1 illustrates an exemplary system for implant health estimation, according to some embodiments of the present disclosure.

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the scope of the disclosed embodiments.

Existing approaches in the domain of implant health detection are targeted to identifying specific anomalies, and there is no system available that determines implant health comprehensively by considering various aspects that may represent health of the implants.

In order to address the aforementioned challenges, a method and system for implant health detection are provided. The method includes obtaining an X-ray image as input. Further, location of an implant in body of a subject is determined by performing implant region localization on the X-ray image. Further, a manufacturer and subtype details of the implant is determined by analyzing the located implant. Further, an implant size is determined by performing a landmark analysis on the located implant. Further, one or more implant fixation details with respect to the implant is determined by analyzing the located implant. Further, an anomaly detection is performed to determine presence of one or more anomalies in the implant, based on the determined manufacturer and subtype details, the determined location of the implant, a determined region around the implant, the one or more implant fixation details, and the implant size information. Further, health of the implant is determined based on the determined presence of anomalies. Determining the health of the implant includes classifying the implant as one of Faulty, Healthy, and Probable faulty.

Referring now to the drawings, and more particularly to FIG. 1 through FIG. 4?, where similar reference characters denote corresponding features consistently throughout the figures, there are shown preferred embodiments and these embodiments are described in the context of the following exemplary system and/or method.

FIG. 1 illustrates an exemplary system for implant health estimation, according to some embodiments of the present disclosure.

The system 100 includes or is otherwise in communication with hardware processors 102, at least one memory such as a memory 104, an I/O interface 112. The hardware processors 102, memory 104, and the Input/Output (I/O) interface 112 may be coupled by a system bus such as a system bus 108 or a similar mechanism. In an embodiment, the hardware processors 102 can be one or more hardware processors.

The I/O interface 112 may include a variety of software and hardware interfaces, for example, a web interface, a graphical user interface, and the like. The I/O interface 112 may include a variety of software and hardware interfaces, for example, interfaces for peripheral device(s), such as a keyboard, a mouse, an external memory, a printer and the like. Further, the I/O interface 112 may enable the system 100 to communicate with other devices, such as web servers, and external databases.

The I/O interface 112 can facilitate multiple communications within a wide variety of networks and protocol types, including wired networks, for example, local area network (LAN), cable, etc., and wireless networks, such as Wireless LAN (WLAN), cellular, or satellite. For the purpose, the I/O interface 112 may include one or more ports for connecting several computing systems with one another or to another server computer. The I/O interface 112 may include one or more ports for connecting several devices to one another or to another server.

The one or more hardware processors 102 may be implemented as one or more microprocessors, microcomputers, microcontrollers, digital signal processors, central processing units, node machines, logic circuitries, and/or any devices that manipulate signals based on operational instructions. Among other capabilities, the one or more hardware processors 102 is configured to fetch and execute computer-readable instructions stored in the memory 104.

The memory 104 may include any computer-readable medium known in the art including, for example, volatile memory, such as static random-access memory (SRAM) and dynamic random-access memory (DRAM), and/or non-volatile memory, such as read only memory (ROM), erasable programmable ROM, flash memories, hard disks, optical disks, and magnetic tapes. In an embodiment, the memory 104 includes a plurality of modules 106.

The plurality of modules 106 include programs or coded instructions that supplement applications or functions performed by the system 100 for executing different steps involved in the process of the implant health estimation. The plurality of modules 106, amongst other things, can include routines, programs, objects, components, and data structures, which performs particular tasks or implement particular abstract data types. The plurality of modules 106 may also be used as, signal processor(s), node machine(s), logic circuitries, and/or any other device or component that manipulates signals based on operational instructions. Further, the plurality of modules 106 can be used by hardware, by computer-readable instructions executed by the one or more hardware processors 102, or by a combination thereof. The plurality of modules 106 can include various sub-modules (not shown). The plurality of modules 106 may include computer-readable instructions that supplement applications or functions performed by the system 100 for the implant health estimation.

The data repository (or repository) 110 may include a plurality of abstracted piece of code for refinement and data that is processed, received, or generated as a result of the execution of the plurality of modules in the module(s) 106.

Although the data repository 110 is shown internal to the system 100, it will be noted that, in alternate embodiments, the data repository 110 can also be implemented external to the system 100, where the data repository 110 may be stored within a database (repository 110) communicatively coupled to the system 100. The data contained within such external database may be periodically updated. For example, new data may be added into the database (not shown in FIG. 1) and/or existing data may be modified and/or non-useful data may be deleted from the database. In one example, the data may be stored in an external system, such as a Lightweight Directory Access Protocol (LDAP) directory and a Relational Database Management System (RDBMS). Functions of the components of the system 100 are now explained with reference to the steps in flow diagrams in FIG. 2 through FIG. 3, and the example architecture diagram in FIG. 4.

Figure 2:
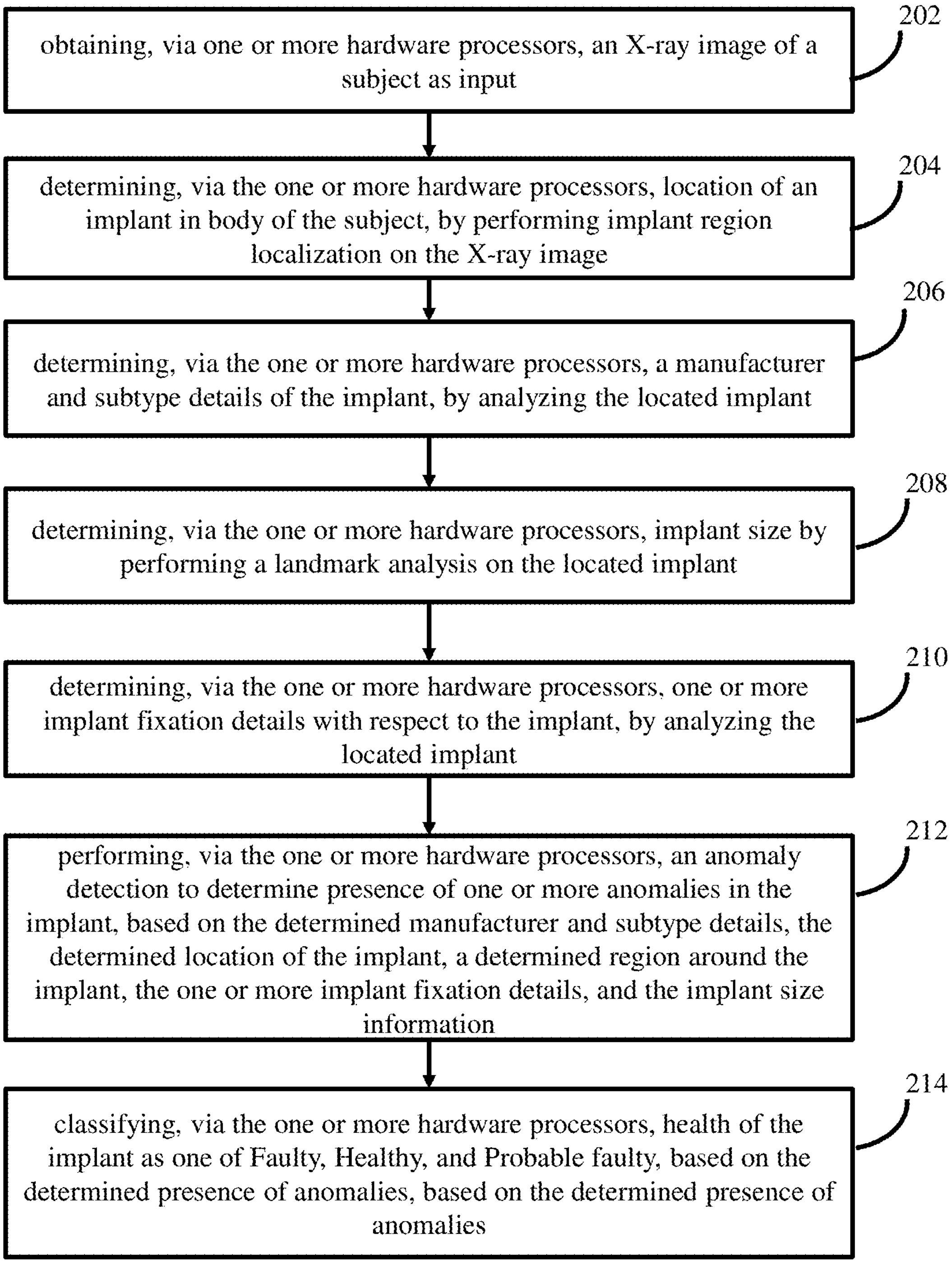
FIG. 2 is a flow diagram depicting steps involved in the process of implant health estimation, by the system of FIG. 1, according to some embodiments of the present disclosure.
Figure 3:
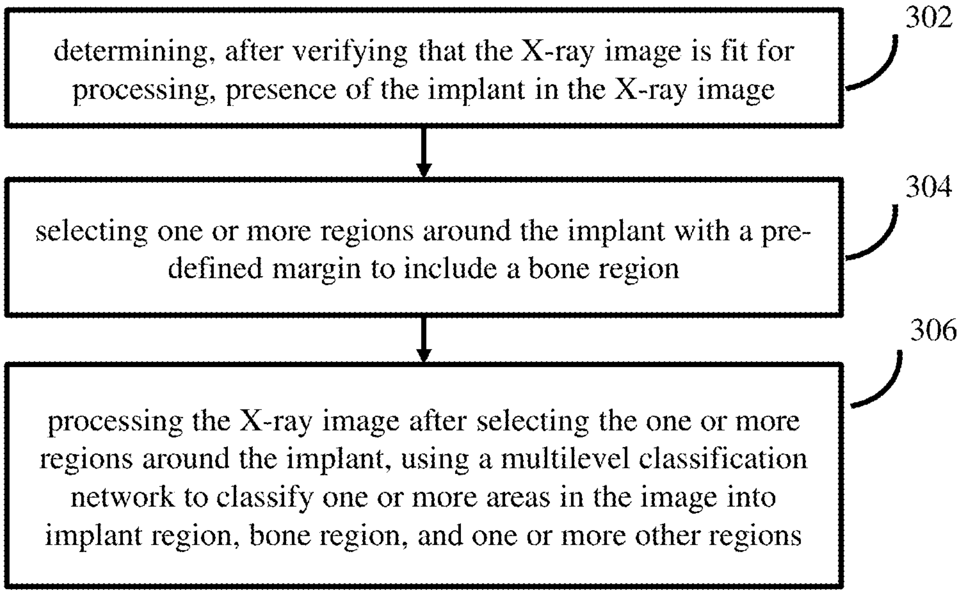
FIG. 3 is a flow diagram depicting steps involved in a process of implant region localization being performed for the implant health estimation, by the system of FIG. 1, according to some embodiments of the present disclosure.

FIG. 2 is a flow diagram depicting steps involved in the process of implant health estimation, by the system of FIG. 1, according to some embodiments of the present disclosure.

In an embodiment, the system 100 comprises one or more data storage devices or the memory 104 operatively coupled to the processor(s) 102 and is configured to store instructions for execution of steps of a method 200 by the processor(s) or one or more hardware processors 102. The steps of the method 200 of the present disclosure will now be explained with reference to the components or blocks of the system 100 as depicted in FIG. 1 and the steps of flow diagram as depicted in FIG. 2. Although process steps, method steps, techniques or the like may be described in a sequential order, such processes, methods, and techniques may be configured to work in alternate orders. In other words, any sequence or order of steps that may be described does not necessarily indicate a requirement that the steps to be performed in that order. The steps of processes described herein may be performed in any order practical. Further, some steps may be performed simultaneously.

At step 202 of a method 200 in FIG. 2, the system 100 obtains an X-ray image of a subject as input. In an embodiment, the X-ray image is collected directly from an X-ray imaging machine that is in communication with the system 100 via appropriate interface. In another embodiment, the subject or any other authorized user may upload the X-ray image to the system 100, using a suitable user interface provided by the system 100.

Further, at step 204 of the method 200, the system 100 determines location of an implant in body of a subject by performing implant region localization on the X-ray image. Throughout the description, terms 'implant' and 'body implant' are interchangeably used. Various steps in the process of implant region localization are depicted in method 300 in FIG. 3, and are explained hereafter. Before performing the implant region localization, the system 100 may verify quality of the X-ray image is fit for processing. In an embodiment, the system 100 may use any suitable image processing technique, for example exposure check, blurriness check, noise etc., using pixel-based method, to determine whether or not the X-ray image is fit for processing. In this example, if the pixel density is below the threshold, the system 100 may consider that the X-ray image is not fit for processing, and may accordingly prompt the subject/user to provide a better clarity image as input. After verifying that the X-ray image is fit for processing, at step 302 of the method 300, the system 100 determines presence of the implant in the X-ray image. At this stage, the system 100 may use a suitable architecture such as but not limited to Mask RCNN or Efficient net, to detect the implant presence and precise location of the implant. Further, at step 304 of the method 300, the system 100 selects one or more regions around the implant with a pre-defined margin to include a bone region. In an embodiment, value of the margin maybe pre-defined or may be dynamically configured with the system 100. Further, at step 306 of the method 300, the system 100 processes the X-ray image after selecting the one or more regions around the implant, using a multilevel classification network such as but not limited to EfficientNet, or Vision Transformers (ViT), to classify one or more areas in the image into implant region, bone region, and one or more other regions.

Referring back to the method 200, at step 206 of the method 200, the system 100 determines, by analyzing the located implant, a manufacturer and subtype details of the implant. In an embodiment, the system 100 uses the approach as detailed in applicant's Indian patent application: 202321049274, for the purpose of determining the manufacturer and subtype details of the implant.

Further, at step 208 of the method 200, the system 100 determines an implant size, i.e., size of the implant, by performing a landmark analysis on the located implant. The system 100 may use a landmark analysis process covered in applicant's Indian Patent Application number 202021021473. At this stage, the system 100 uses a landmark based approach for determining the implant size, in which, the system 100 determines, with respect to a plurality of landmarks, metrics such as but not limited to length, and angles, and then based on the determined metrics and associated values, determines the size of the implant.

Figure 4:
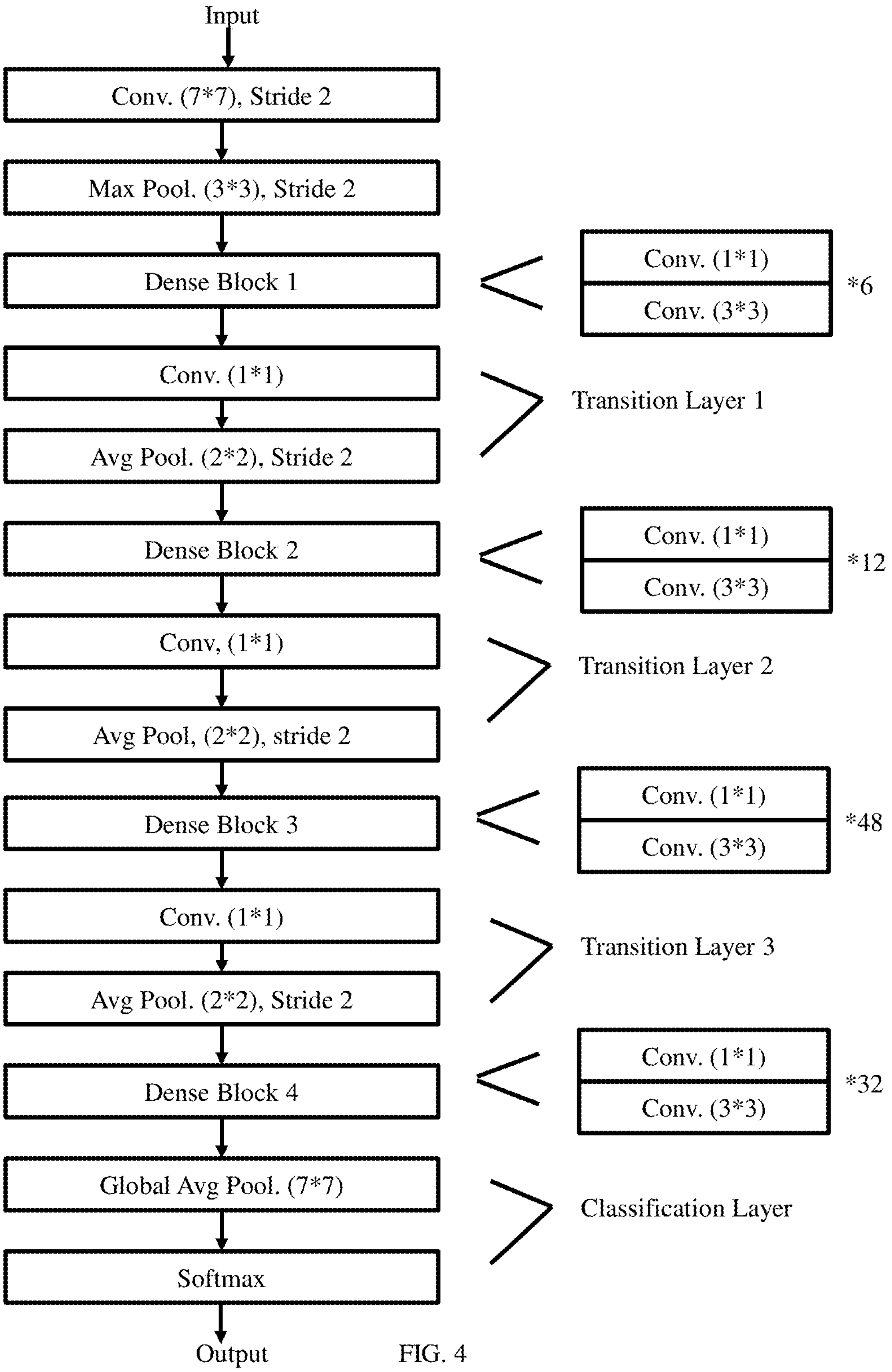
FIG. 4 depicts an architecture used for determining one or more implant fixation details, by the system of FIG. 1, according to some embodiments of the present disclosure.

Further, at step 210 of the method 200, the system 100 determines, via the one or more hardware processors 102, one or more implant fixation details with respect to the implant, by analyzing the located implant. The one or more implant fixation details refers to categorization of the implant as one of cemented, uncemented, and hybrid hip replacements. The one or more implant fixation details enables an authorized user, for example a doctor, to determine a choice of replacement type, which depends on factors such as bone health, patient age, and activity level. Additionally, identifying the type of replacement, along with the implant subtype and manufacturer, can make a revision surgery much easier for the surgeon. The system 100 may detect sub-classes such as, but not limited to, cemented bipolar, uncemented bipolar, hemiarthroplasty, and reverse hybrid. In an embodiment, the system 100 may use a suitable architecture, for example, the architecture as depicted in FIG. 4. An experiment was conducted using a pretrained DenseNet 201 network with an added a classification layer at the end to modify it for 3-class classification as in FIG. 4. The data was split into training, validation, and testing datasets in a 70:15:15 ratio. This accuracy was reported after performing four cross-validations. This experiment provided an accuracy in the range of 85-90 percent.

Further, at step 212 of the method 200, the system 100 performs an anomaly detection to determine presence of one or more anomalies in the implant, based on the determined manufacturer and subtype details, the determined location of the implant, a determined region around the implant, and the implant size information. Some of the anomalies that are determined by the system are, but not limited to radiolucency, metrics based implant loosening, and implant breakages. In order to locate the radiolucency, the system 100 analyzes texture features such as wavelets and gray-level co-occurrence matrix (GLCM) around the determined bone region. The radiolucency, if present, is an indication of implant becoming loose. In order to locate metrics-based implant loosening, i.e. sinking detection, the system 100 checks for historical patient implant images available in an associated database. In an embodiment, the historical patient implant images is for the same patient for whom the implant health detection is being performed. Further, if one or more historical images are obtained from the historical data, the system 100 then locates the implant region in the one or more historical image, and then obtains critical landmarks from the one or more historical images as well as from the X-ray image that has been obtained as input, using a landmark detection technique as elaborated in applicant's Indian Patent Application number 202021021473. Further, the system 100 derives the metrics such as length from one region to another, angles and so on. Further, based on the derived metrics, the system 100 compares the input X-ray image with one or more of the historical images to check for discrepancies. If there is a change in position of the implant with reference to a determined position of the implant in the historical images, the system 100 infers that the implant is sinking and is becoming loose. In another approach, the system 100 obtains an original implant template for the identified implant manufacturer and the subtype. The system 100 has in associated historical database, history of known defects from the manufacturer, and for the identified subtype. The system 100 checks and determines if the obtained X-ray image of the implant has any character that matches with a failure or breakage of the implant as being inferred from the historical images, and if yes, then infers/identifies a possible implant breakage condition. The system 100 determines the implant breakage based on a template based anomaly detection, and one or more image processing algorithms. Some examples of the image processing algorithms are change detection algorithms and breakage detection algorithms. Also, at this stage, one or more inferences from the one or more implant fixation details maybe provided along with the information on the detected one or more anomalies, so that a user maybe able to make an informed decision with respect to one or more actions to be performed (for example, surgery to be performed, tools required, replacement implant to be selected and so on).

Further, at step 214 of the method 200, the system 100 classifies the implant as one of Faulty, Healthy, and Probable faulty, based on the determined presence of anomalies. For example, if the implant breakage and/or the radiolucency and/or the implant sinking has been detected at step 212 of the method 200, then the system 100 determines the implant as faulty. If none of the aforementioned conditions is determined, then the system 100 identifies the implant as healthy. In an embodiment, if from the historical data the system 100 determines an implant location change and/or sinking conditions, however of the original image is not available, then the system 100 may not be able to conclude that the implant is faulty or healthy, and in this scenario, the system 100 identifies the implant as partially faulty, and may accordingly flag it for further inspection/verification. By classifying the health of the implant as one of the Faulty, Healthy, and Probable faulty, the system 100 determines the health of the implant, which is an estimation of the health of the implant, hence the method 200 is termed as implant health estimation.

The system 100 may indicate to a user of the system 100, via appropriate interface, what is the determined health condition of the implant. Especially if the implant is determined as partially faulty or faulty, the system 100 may trigger alarms of pre-defined type to notify one or more users to take appropriate corrective actions (for example, implant replacement) or may conduct further inspection/verification.

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

The embodiments of present disclosure herein address unresolved problem of implant health detection. The embodiment thus provides a mechanism to identify a variety of anomalies with the implant. Moreover, the embodiments herein further provides a mechanism to categorize the implant into a specific category representing the health of the implant.

It is to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g., any kind of computer like a server or a personal computer, or the like, or any combination thereof. The device may also include means which could be e.g., hardware means like e.g., an application-specific integrated circuit (ASIC), a field-programmable gate array (FPGA), or a combination of hardware and software means, e.g., an ASIC and an FPGA, or at least one microprocessor and at least one memory with software processing components located therein. Thus, the means can include both hardware means and software means. The method embodiments described herein could be implemented in hardware and software. The device may also include software means. Alternatively, the embodiments may be implemented on different hardware devices, e.g., using a plurality of CPUs.

The embodiments herein can comprise hardware and software elements. The embodiments that are implemented in software include but are not limited to, firmware, resident software, microcode, etc. The functions performed by various components described herein may be implemented in other components or combinations of other components. For the purposes of this description, a computer-usable or computer readable medium can be any apparatus that can comprise, store, communicate, propagate, or transport the program for use by or in connection with the instruction execution system, apparatus, or device.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope of disclosed embodiments being indicated by the following claims.

What is claimed is:

1. A processor implemented method, comprising:

obtaining, via one or more hardware processors, an X-ray image of a subject as input;

determining, via the one or more hardware processors, a location of an implant in body of the subject, by performing implant region localization on the X-ray image;

determining, via the one or more hardware processors, a manufacturer and subtype details of the implant, by analyzing the located implant;

determining, via the one or more hardware processors, implant size by performing a landmark analysis on the located implant;

determining, via the one or more hardware processors, one or more implant fixation details with respect to the implant, by analyzing the located implant;

performing, via the one or more hardware processors, an anomaly detection to determine presence of one or more anomalies in the implant, based on the determined manufacturer and subtype details, the determined location of the implant, a determined region around the implant, the one or more implant fixation details, and the implant size information; and classifying, via the one or more hardware processors, health of the implant as one of Faulty, Healthy, and Probable faulty, based on the determined presence of anomalies.

2. The method of claim 1, wherein performing the implant region localization comprises:

determining, after verifying that the X-ray image is fit for processing, presence of the implant in the X-ray image;

selecting one or more regions around the implant with a pre-defined margin to include a bone region; and processing the X-ray image after selecting the one or more regions around the implant, using a multilevel classification network to classify one or more areas in the image into implant region, bone region, and one or more other regions.

3. The method of claim 1, wherein the one or more anomalies comprises implant loosening, and implant breakage, wherein, the implant loosening is determined based on one of a) presence of radiolucency around the implant, and b) a metrics based data from one or more history images, and the implant breakage is determined based on one of a) a template based anomaly detection, and b) one or more image processing algorithms for anomaly detection.

4. A system, comprising:

one or more hardware processors;

a communication interface; and a memory storing a plurality of instructions, wherein the plurality of instructions cause the one or more hardware processors to:

obtain an X-ray image of a subject as input;

determine a location of an implant in body of a subject, by performing implant region localization on the X-ray image;

determine a manufacturer and subtype details of the implant, by analyzing the located implant;

determine implant size by performing a landmark analysis on the located implant;

determine one or more implant fixation details with respect to the implant, by analyzing the located implant;

perform an anomaly detection to determine presence of one or more anomalies in the implant, based on the determined manufacturer and subtype details, the determined location of the implant, a determined region around the implant, the one or more implant fixation details, and the implant size information; and classify health of the implant as one of Faulty, Healthy, and Probable faulty, based on the determined presence of anomalies.

5. The system as claimed in claim 4, wherein the one or more hardware processors are configured to perform the implant region localization by:

determining, after verifying that the X-ray image is fit for processing, presence of the implant in the X-ray image;

selecting one or more regions around the implant with a pre-defined margin to include a bone region; and processing the X-ray image after selecting the one or more regions around the implant, using a multilevel classification network to classify one or more areas in the image into implant region, bone region, and one or more other regions.

6. The system as claimed in claim 4, wherein the one or more anomalies comprises implant loosening, and implant breakage, wherein, the implant loosening is determined based on one of a) presence of radiolucency around the implant, and b) a metrics based data from one or more history images, and the implant breakage is determined based on one of a) a template based anomaly detection, and b) one or more image processing algorithms for anomaly detection.

7. One or more non-transitory machine-readable information storage mediums comprising one or more instructions which when executed by one or more hardware processors cause:

obtaining an X-ray image of a subject as input;

determining a location of an implant in body of the subject, by performing implant region localization on the X-ray image;

determining a manufacturer and subtype details of the implant, by analyzing the located implant;

determining implant size by performing a landmark analysis on the located implant;

determining one or more implant fixation details with respect to the implant, by analyzing the located implant;

performing an anomaly detection to determine presence of one or more anomalies in the implant, based on the determined manufacturer and subtype details, the determined location of the implant, a determined region around the implant, the one or more implant fixation details, and the implant size information; and classifying health of the implant as one of Faulty, Healthy, and Probable faulty, based on the determined presence of anomalies.

8. The one or more non-transitory machine-readable information storage mediums as claimed in claim 7, wherein performing the implant region localization comprises:

determining after verifying that the X-ray image is fit for processing presence of the implant in the X-ray image;

selecting one or more regions around the implant with a pre-defined margin to include a bone region; and processing the X-ray image after selecting the one or more regions around the implant, using a multilevel classification network to classify one or more areas in the image into implant region, bone region, and one or more other regions.

9. The one or more non-transitory machine-readable information storage mediums as claimed in claim 7, wherein the one or more anomalies comprises implant loosening, and implant breakage, wherein, the implant loosening is determined based on one of a) presence of radiolucency around the implant, and b) a metrics based data from one or more history images, and the implant breakage is determined based on one of a) a template based anomaly detection, and b) one or more image processing algorithms for anomaly detection.

* * * * *